(12) United States Patent
Beller et al.

(10) Patent No.: US 7,115,790 B2
(45) Date of Patent: Oct. 3, 2006

(54) METHOD FOR THE PRODUCTION OF 1-OCTENE BY REDUCTIVE TELOMERISATION

(75) Inventors: Matthias Beller, Nienhagen (DE); Ralf Jackstell, Cuxhaven (DE); Holger Klein, Rostock (DE); Dirk Roettger, Recklinghausen (DE); Dietrich Maschmeyer, Recklinghausen (DE); Silvia Santiago Fernandez, Oberhausen (DE)

(73) Assignee: OXENO Olefinchemie GmbH, Marl (DE)

( * ) Notice: Subject to any disclaimer, the term of this patent is extended or adjusted under 35 U.S.C. 154(b) by 60 days.

(21) Appl. No.: 10/497,034

(22) PCT Filed: Sep. 18, 2002

(86) PCT No.: PCT/EP02/10579

§ 371 (c)(1),
(2), (4) Date: Oct. 28, 2004

(87) PCT Pub. No.: WO03/031378

PCT Pub. Date: Apr. 17, 2003

(65) Prior Publication Data

US 2005/0065387 A1   Mar. 24, 2005

(30) Foreign Application Priority Data

Oct. 6, 2001 (DE) ............... 101 49 347

(51) Int. Cl.
C07C 2/76 (2006.01)

(52) U.S. Cl. .......... 585/324; 585/601; 585/271
(58) Field of Classification Search ........ 585/324, 585/601, 271
See application file for complete search history.

(56) References Cited

U.S. PATENT DOCUMENTS

| | | | |
|---|---|---|---|
| 3,317,634 A * | 5/1967 | Longworth | ......... 525/263 |
| 6,627,782 B1 | 9/2003 | Kaizik et al. | |
| 2004/0059170 A1 | 3/2004 | Rottger et al. | |

FOREIGN PATENT DOCUMENTS

| | | |
|---|---|---|
| EP | 012 472 | 6/1980 |
| EP | 621 288 | 10/1994 |
| WO | 92/10450 | 6/1992 |

OTHER PUBLICATIONS

U.S. Appl. No. 10/490,038, filed Mar. 19, 2004, Beller et al.
U.S. Appl. No. 10/478,697, filed Dec. 9, 2003, Rottger et al.
U.S. Appl. No. 10/538,475, filed Jun. 7, 2005, Kaizik et al.
U.S. Appl. No. 10/538,359, filed Jun. 13, 2005, Rottger et al.
U.S. Appl. No. 10/517,620, filed Dec. 23, 2004, Rottger et al.
U.S. Appl. No. 10/470,280, filed Aug. 8, 2003, Rottfer et al.

* cited by examiner

*Primary Examiner*—Thuan Dinh Dang
(74) *Attorney, Agent, or Firm*—Oblon, Spivak, McClelland, Maier & Neustadt, P.C.

(57) ABSTRACT

The invention relates to a process for preparing 1-octene by telomerization of 1,3-butadiene using a reducing agent in the presence of a telomerization catalyst and partial hydrogenation of the octadiene obtained in this way.

15 Claims, No Drawings

METHOD FOR THE PRODUCTION OF 1-OCTENE BY REDUCTIVE TELOMERISATION

BACKGROUND OF THE INVENTION

1. Field of the Invention

The invention relates to a process for preparing 1-octene by telomerization of 1,3-butadiene using a reducing agent in the presence of a telomerization catalyst and partial hydrogenation of the octadiene obtained in this way.

2. Description of the Background

1-Octene is used in large quantities in the production of various chemical products. For example, surface-active substances, plasticizers, lubricants and polymers are produced from 1-octene. Another large application area is its use as comonomer in polymers, in particular in polyethylene. Virtually all processes utilized commercially at present for producing 1-octene are based on ethene as raw material. Ethene is oligomerized to give a spectrum of $\alpha$-olefins as main products. If the catalyst and process conditions are chosen appropriately, the amount of 1-octene in the product can be optimized and is then about 25%. Apart from this process, by means of which most of the 1-octene produced is obtained, isolation of 1-octene from the spectrum of products from the Fischer-Tropsch reaction has achieved some importance.

Apart from the processes based on ethene, processes using 1,3-butadiene as raw material for preparing 1-octene are also known from the literature. However, 1-octene cannot be obtained directly, for example via dimerization, from butadiene, but is obtained after a plurality of process steps. 1,3-Butadiene is usually reacted catalytically with a telogen to form a telomer which is fully or partially hydrogenated and subsequently subjected to a cleavage reaction to give the desired 1-octene.

Thus, the patent application WO 92/10450 describes a process in which 1,3-butadiene is reacted with, preferably, methanol or ethanol to form a 2,7-octadienyl ether which, after hydrogenation to the octyl ether, is cleaved to give 1-octene. An analogous route is employed in EP-A-0 440 995, but the reaction in the first step is with a carboxylic acid. The first process step, which is generally referred to as a telomerization, is common to the processes. In the telomerization, a telogen (in EP-A-0 440 995, the carboxylic acid) is generally reacted with a taxogen (1,3-butadiene, 2 equivalents) to form a telomer.

Processes for the catalytic preparation of 1,7-octadienes from 1,3-butadiene have likewise been described in the literature. Thus, EP 12475 and EP 12472 disclose a process for preparing 1,7-octadiene in which butadiene is reacted reductively with formic acid or formates in the presence of organophosphonites and palladium, optionally together with further ligands, to form 1,7-octadiene. Similar processes are described by Raffia et al. in J. Organometal. Chem. 55 (1973), 405–407, who use triphenylphosphine and Pittmann et al. (J. Mol. Chem. 15 (1982) 377–381) who use triethylphosphine and triethylamine as ligands for palladium. The preparation of a 1-olefin is not disclosed in these references.

SUMMARY OF THE TNVENTION

It is therefore an object of the invention to discover a process by means of which 1-octene can be prepared from 1,3-butadiene and which makes do without the abovementioned cleavage step and gives 1-octene in good yields and selectivity.

It has been found that 1-octene can be obtained in good yield and selectivity from a reductive telomerization process with subsequent hydrogenation.

The invention accordingly provides a process for preparing 1-octene, in which
a) 1,3-butadiene is reacted in the presence of a telomerization catalyst and a reducing agent to form 1,7-octadiene and
b) the resulting 1,7-octadiene is hydrogenated to give 1-octene.

DETAILED DESCRIPTION OF THE PREFERRED EMBODIMENTS

The telomerization process in step a) of the present invention can be carried out using either pure 1,3-butadiene or mixtures in which 1,3-butadiene is present. As 1,3-butadiene-containing mixtures, preference is given to using mixtures of 1,3-butadiene with other $C_4$-hydrocarbons. Such mixtures are obtained, for example, in cracking processes for the production of ethene, in which refinery gases, naphtha, gas oil, LPG (liquefied petroleum gas), NGL (natural gas liquid), etc., are used as feedstocks. The $C_4$ fractions obtained as by-product in these processes contain varying amounts of 1,3-butadiene which depend on the cracking process. Typical 1,3-butadiene concentrations in the $C_4$ fraction as obtained from a naphtha steam cracker are 20–70% of 1,3-butadiene.

The $C_4$ components n-butane, i-butane, 1-butene, cis-2-butene trans-2-butene and i-butene which are likewise present in these fractions do not interfere or do not interfere significantly in the reaction in the telomerization step. However, dienes having cumulated double bonds (1,2-butadiene, allene, etc.) and alkynes, in particular vinylacetylene, can act as moderators in the telomerization reaction. It is therefore advantageous to remove the $C_4$-alkynes and, if appropriate, the 1,2-butadiene beforehand. This may, if possible, be carried out by physical methods such as distillation or extraction. A possible chemical route is selective hydrogenation to convert the alkynes into alkenes or alkanes and convert the cumulated dienes into monoenes. Processes for such hydrogenations are prior art and are described, for example, in WO 98/12160, EP-A-0 273 900, DE-A-37 44 086 or U.S. Pat. No. 4,704,492.

As telomerization catalysts, it is possible to use homogeneous, heterogeneous or immobilized catalysts or combinations thereof. The literature describes many catalysts for this reaction (cf. A. Behr, "Homogeneous Transition Metal Catalysts", Aspects of Homogeneous Catalysis, 1984, 5, 3–73). For example, transition metals from group VIII of the Periodic Table of the Elements and their complexes are successfully used as catalysts.

For the purposes of the present invention, the use of nickel, rhodium, palladium and platinum catalysts as telomerization catalyst is preferred.

Particular preference is given to using palladium catalysts. It is possible to use either palladium(0) or palladium (II) compounds in the telomerization step.

Examples of suitable palladium compounds are palladium (II) chloride, palladium(II) bromide, palladium(II) acetate, palladium(II) formate, palladium(II) octanoate, palladium (II) carbonate, palladium(II) sulfate, palladium(II) nitrate, palladium(II) acetylacetonate, palladium(II) alkylsulfonate, $Na_2PdCl_4$, $K_2PdCl_4$, dichlorobis(benzonitrile)palladium, allylpalladium chloride, allylpalladium acetate, trisallylpalladium, 1,5-cyclo-octadienepalladium(II) chloride, bis (triphenylphosphine)palladium(II) chloride, (1,2-bis(diphenylphosphino)ethane)palladium(II) chloride. When using palladium halides, an activator may have to be added to the reaction, since free halide ions can inhibit the telomerization reaction. The use of palladium(II) salts of organic acids, e.g. palladium acetate or palladium acetylacetonate, is therefore preferred. Examples of palladium(0) complexes include complexes of palladium with phosphorus, nitrogen or arsenic donor atoms, alkyne, alkene and diene complexes and palladium-carbene complexes. Examples of phosphorus ligands are phosphines, phosphites, phosphonites and phosphinites, while examples of nitrogen ligands are amines, nitriles and pyridines. Specific examples are tetrakis-(triphenylphosphine)palladium(0), tris(dibenzylideneacetone)dipalladium(0) and bis(1,5-cyclooctadiene)palladium. Examples of carbene ligands which coordinate to palladium are 1,3-disubstituted 2,3-dihydro-1H-imidazol-2-ylidenes.

The amount of telomerization catalyst used depends on its activity. In principle, it is possible to use any amount of catalyst which ensures a sufficient reaction rate. In homogeneously catalyzed reactions in which starting materials, products and a transition metal catalyst are present in dissolved form in a single phase, use is generally made of from 0.1 ppm to 50 000 ppm of metal (based on the reaction mixture). When palladium catalysts are used, preference is given to using from 1 ppm to 1 000 ppm, particularly preferably from 3 ppm to 100 ppm, of catalyst metal.

If the telomerization is carried out in multiphase systems (for example heterogeneously catalyzed or in the presence of two liquid phases of which one comprises the catalyst), these concentration ranges can alter. In the case of telomerization in a plurality of liquid phases, it is particularly advantageous for catalyst and product to be present in different phases, since the catalyst can then be separated off in a simple fashion by phase separation. In such a case, water often forms one of the liquid phases. However, use is also made of, for example, perfluorinated hydrocarbons, ionic liquids and supercritical carbon dioxide (on the subject of ionic liquids, of P. Wasserscheid, W. Keim, Angew. Chem., Int. Ed. 2000, 39, 3772–3789). The telomerization of butadiene using water in ionic liquids is described by J. E. L. Dullius, P. A. Z. Suarez, S. Einloft, R. F. de Souza, J. Dupont, J. Fischer, A. D. Cian, Organometallics 1999, 17, 997–1000. A review of the use of water as carrier phase for the catalyst may be found, for example, in B. Cornils, W. A. Herrmann (Eds.) "Aqueous-Phase Organometallic Catalysis", Wiley-VCH, Weinheim, New-York, Chichester, Brisbane, Singapore, Toronto, 1998, pages 442–446. In processes in which a plurality of liquid phases are present, it is particularly advantageous to use a telogen which is present together with the catalyst in one phase while the products are mainly present in a second phase.

The telomerization catalyst can be introduced in active form into the process. However, it is often simpler to use a precursor which forms the catalytically active species under the reaction conditions.

The telomerization reaction can generally be favorably influenced by addition of ligands to the reaction. It is therefore advantageous to carry out step a) of the process of the invention in the presence of the abovementioned metals and of one or more (different) ligands. In principle, all ligands which increase the reaction rate, improve the selectivity, increase the operating life of the catalyst, etc., are suitable. Examples of suitable ligands are compounds containing one or more trivalent phosphorus, arsenic, antimony or nitrogen atoms. Particularly useful types of compounds are phosphines, phosphonites, amines, nitriles and carbenes.

Examples of phosphorus ligands are:
phosphines such as triphenylphosphine, tris(p-tolyl)phosphine, tris(m-tolyl)phosphine, tris(o-tolyl)phosphine, tris(p-methoxyphenyl)phosphine, tris(p-dimethylaminophenyl) phosphine, tricyclohexylphosphine, tricyclopentylphosphine, triethylphosphine, tris-(1-naphthyl)phosphine, tribenzylphosphine, tri-n-butylphosphine, tri-tert-butylphosphine, tris-(3-sulfonatophenyl)phosphine (metal salt), bis(3-sulfonatophenyl)phenylphosphine (metal salt), (3-sulfonatophenyl)diphenylphosphine (metal salt), phosphites such as trimethyl phosphite, triethyl phosphite, tri-n-propyl phosphite, tri-i-propyl phosphite, tri-n-butyl phosphite, tri-i-butyl phosphite, tri-tert-butylphosphite, tris (2-ethylhexyl) phosphite, triphenyl phosphite, tris(2,4-di-tert-butylphenyl)phosphite, tris(2-tert-butyl-4-methoxyphenyl) phosphite, tris(2-tert-butyl-4-methylphenyl) phosphite, tris(p-cresyl) phosphite, phosphonites such as methyldiethoxyphosphine, phenyldimethoxyphosphine, phenyidiphenoxyphosphine, 2-phenoxy-2H-dibenz[c,e][1,2]oxaphosphorin and their derivatives in which some or all of the hydrogen atoms are replaced by alkyl and/or aryl radicals or halogen atoms, phosphinites such as diphenyl(phenoxy) phosphine and its derivatives in which some or all of the hydrogen atoms are replaced by alkyl and/or aryl radicals or halogen atoms, diphenyl(methoxy)phosphine, diphenyl (ethoxy)-phosphine, etc.

For the purposes of the present invention, phosphonium salts can also act as ligands. Examples of suitable phosphonium salts and their use in telomerization may be found, inter alia, in EP-A-0 296 550.

Examples of carbene ligands in the telomerization catalyst are carbenes in which the carbene carbon is bound to two nitrogen atoms, as, for example, in 1,3-disubstituted 2,3-dihydro-1H-imidazol-2-ylidene or 1,3-disubstituted 4,5-dihydro-1H-triazol-5-ylidenes. Substituted or unsubstituted 2,3-dihydrothiazol-2-ylidenes can also be used as carbene ligands.

When carbene ligands are used, preference is given to using palladium as catalyst metal.

The ratio of ligand to metal (mol/mol) is normally from 0.1/1 to 500/1, preferably from 0.5/1 to 50/1, particularly preferably from 1/1 to 20/1. The ligand can be added to the reaction as such, in dissolved form or in the form of metal complexes. Additional ligand can be added to the reaction at any point in time and at any point in the reactor either as such, as a solution or in the form of a metal complex.

The reaction is carried out in the presence of reducing agents. Preferred reducing agents are hydrogen, formic acid and/or formates. The reducing agents are not nucleophiles or telogens in the telomerization reaction.

Examples of formates are ammonium formate, organic salts such as triethylammonium formate, trimethylammonium formate, tripropylammonium formate and alkali metal and alkaline earth metal salts such as lithium formate, sodium formate, potassium formate, magnesium formate and calcium formate. The formates can be added to the reaction either as such or in dissolved form or can be prepared in situ. Thus, the alkali metal formates can be prepared from the reaction of formic acid with the metal hydroxides, but can also be prepared from metal hydroxides and carbon monoxide. As source of carbon monoxide, it is possible to use gases comprising carbon monoxide, for example synthesis gas ($H_2$/CO mixture).

The formation of one mole of 1,7-octadiene from two mol of butadiene requires one mol of formic acid or formate (stoichiometry of the reaction). Depending on the way in which the reaction is carried out, the total amount and, if desired, an excess of reducing agent can all be added at the beginning of the reaction. As an alternative, the reducing agent can be metered in over the course of the reaction.

The ratio of formic acid or formate to 1,3-butadiene in the reactor is therefore preferably from 100/1 to 1/100, particularly preferably from 10/1 to 1/10.

If hydrogen is used as reducing agent, the partial pressure is from 1 to 300 bar, preferably from 1 to 64 bar. The hydrogen is employed in pure form or as a mixture with other gases, for example carbon dioxide or nitrogen.

It is possible to use a plurality of reducing agents side by side, for example formic acid and hydrogen.

It is often advantageous to carry out the telomerization reaction in the presence of bases. Examples of suitable bases are metal hydroxides, in particular alkali metal hydroxides and alkaline earth metal hydroxides, metal carbonates and metal hydrogencarbonates, in particular alkali metal and alkaline earth metal carbonates and alkali metal and alkaline earth metal hydrogen carbonates, hydroxides of quaternary ammonium or phosphonium ions, alkoxides, enolates, phenoxides, metal salts of carboxylic acids, metal amides such as sodium amide or lithium diethylamide, alkali metal borohydrides, alkali metal aluminum hydrides and organic nitrogen bases, in particular amines such as triethylamine, pyridine or trioctylamine. Carbon dioxide can also be used as base. The amount of base added to the telomerization reaction is strongly dependent on the type of base used. When using transition metal catalysts, it is normal to use from 0 to 50 000 mol of base per mole of transition metal, preferably from 0.5 to 5 000 mol, particularly preferably from 0.5 to 500 mol, of base per mole of transition metal. It is also possible to use a plurality of bases at once.

The addition of other auxiliaries can bring advantages in carrying out step a) of the process of the invention. An example is the use of inhibitors which suppress the polymerization of butadiene. Such inhibitors are normally present in commercial, (stabilized) pure 1,3-butadiene. A standard stabilizer is, for example, tert-butylcatechol.

Step a) of the process of the invention can be carried out without solvents or with addition of solvents. The solvents used should be largely inert. Suitable solvents include aliphatic, cycloaliphatic and aromatic hydrocarbons such as $C_3$–$C_{20}$-alkanes, mixtures of lower or higher alkanes ($C_3$–$C_{20}$), cyclohexane, cyclooctane, ethyl cyclohexane, alkenes and polyenes, vinylcyclohexene, 1,3,7-octatriene, the $C_4$-hydrocarbons from $C_4$ fractions from crackers, benzene, toluene and xylene; polar solvents such as tertiary and secondary alcohols, amides such as acetamide, dimethylacetamide and dimethylformamide, nitriles such as acetonitrile and benzonitrile, ketones such as acetone, methyl isobutyl ketone and diethyl ketone, carboxylic esters such as ethyl acetate, ethers such as dipropyl ether, diethyl ether, methyl tert-butyl ether (MTBE), dimethyl ether, methyl octyl ether, 3-methoxyoctane, dioxane, tetrahydrofuran, anisole, alkyl and aryl ethers of ethylene glycol, diethylene glycol and polyethylene glycol and other polar solvents such as sulfolane, dimethyl sulfoxide, ethylene carbonate and propylene carbonate. Water can also be used as solvent.

The solvents are used either alone or as mixtures of various solvents.

Step a) of the present invention is advantageously carried out with exclusion of oxygen, since oxygen has an adverse effect on the stability of the catalyst systems. The temperature at which the telomerization reaction is carried out is in the range from 10° C. to 200° C., preferably from 40° C. to 150° C., particularly preferably from 40° C. to 110° C. The reaction pressure is from 1 bar to 300 bar, preferably from 1 bar to 120 bar, particularly preferably from 1 bar to 64 bar and very particularly preferably from 1 bar to 20 bar.

In the process of the invention, it is not necessary to achieve complete conversion of the butadiene in the telomerization reaction. The conversion of butadiene is therefore preferably in the range from 5% to 100%, particularly preferably from 50% to 100%, very particularly preferably from 80% to 100%.

Step a) of the process of the invention can be carried out continuously or batchwise and is not restricted to the use of particular types of reactor. Examples of reactors in which the reaction can be carried out are stirred tank reactors, cascades of stirred tanks, flow tubes and loop reactors. Combinations of various reactors are also possible, for example a stirred tank reactor with a downstream flow tube.

The heat of reaction evolved in the reaction is removed by known methods, for example by means of internal or external coolers. Specifically, this can mean the use of shell-and-tube reactors, reactors equipped with cooling fingers, cooling coils or plates or cooling of a recycle stream.

The telomerization catalyst used in step a) of the process of the invention can be recovered after the telomerization reaction and all or some of it can be used for further telomerization reactions (cf. EP-A-0 218 100). The catalyst can be separated off by, for example, distillation, extraction, precipitation or adsorption. If all or some of the catalyst is present in a second phase, it can be separated off in a simple fashion by separation of the phases.

It is also possible for the catalyst to be modified before it is separated off or during the separation. This applies analogously to its return in full or in part to the process, which can likewise be preceded by modification of the catalyst. For example, U.S. Pat. No. 4,146,738 describes a process in which the catalyst is stabilized by auxiliaries prior to being separated off. After separation from the other products, it is activated and returned to the process.

As an alternative, the catalyst can be worked up in other ways after the reaction (cf. WO 90/13531, U.S. Pat. No. 5,254,782).

The 1,7-octadiene obtained in step a) is hydrogenated in step b).

The hydrogenation can be carried out as a liquid-phase or gas-phase hydrogenation or as a combination of these techniques, and can be carried out in one or more steps, for example a preliminary hydrogenation and a final hydrogenation.

The hydrogenation can be carried out continuously or batchwise. As reactors, it is possible to use the known standard reactors for hydrogenations, for example trickle-bed reactors. The heat of reaction evolved in the reaction is removed by known methods, for example by means of internal or external coolers. Specifically, this can mean the use of shell-and-tube reactors, cooling fingers, cooling coils or plates or cooling of a recycle stream.

The hydrogenation is carried out in the presence of a catalyst. It is possible to use either homogeneous or heterogeneous catalysts. For example, the catalyst can comprise at least one element of transition group VIII. If desired, further transition metals can also be used as catalysts for this hydrogenation, in particular copper and/or chromium, if appropriate together with at least one metal of transition group VIII of the Periodic Table.

When using homogeneous catalysts, additional ligands are employed together with the catalyst metal. Suitable ligands are, for example, compounds of trivalent phosphorus (for example phosphines or phosphites), compounds of trivalent arsenic or antimony, nitrogen compounds (for example amines, pyridines, nitrites), halides, carbon monoxide and cyanide.

In the case of heterogeneous catalysts, the abovementioned metals can be modified with other metals or moderators. Thus, for example, the activity and selectivity of heterogeneous palladium catalysts are often modified by addition of sulfur or carbon monoxide. Copper catalysts are often modified by-addition of a proportion of chromium.

The use of supported catalysts is generally advantageous, since smaller amounts of metal are required and it is additionally possible to influence the properties of the catalyst via the nature of the support. Support materials which have been found to be useful are, for example, activated carbon, aluminum oxide, silicon dioxide, silicon aluminum oxide, barium carbonate, barium sulfate and Kieselguhr.

The hydrogenations are carried out at temperatures of from 0 to 400° C., preferably from 20 to 200° C. The pressure is in the range from 0.01 to 300 bar, preferably from 0.1 to 125 bar, particularly preferably from 1 to 64 bar.

The hydrogenation in the liquid phase can, regardless of whether it is homogeneously or heterogeneously catalyzed, be carried out without solvents or in the presence of additional solvents. Examples of suitable solvents are aliphatic and cycloaliphatic hydrocarbons such as $C_3$–$C_{16}$-alkanes, mixtures of lower or higher alkanes ($C_3$–$C_{20}$), cyclohexane, cyclooctane and ethylcyclohexane; alcohols such as methanol, ethanol, propanol, isopropanol, n-butanol, isobutanol, 2-ethylhexanol, isononanol and isotridecanol; polyols such as ethylene glycol, propylene glycol, 1,3-propanediol and 1,4-butanediol; carboxylic esters such as ethyl acetate; ethers such as dipropyl ether, diethyl ether, dimethyl ether, methyl tert-butyl ether, methyl octyl ether, 3-methoxyoctane, dioxane, tetrahydrofuran, alkyl ethers of ethylene glycol, diethylene glycol and polyethylene glycol; sulfolane, dimethyl sulfoxide, ethylene carbonate, propylene carbonate and water. The solvents are used either alone or as mixtures of various solvents.

When the hydrogenation is carried out in the liquid phase, it is possible for a plurality of liquid phases to be present. This variant is particularly advantageous when catalyst and product are present in different phases, since the catalyst can then be separated off in a simple fashion by means of a phase separation. Water often forms one of the liquid phases. However, use is also made of, for example, perfluorinated hydrocarbons, ionic liquids and supercritical carbon dioxide (on the subject of ionic liquids, cf. P. Wasserscheid, W. Keim, Angew. Chem., Int. Ed. 2000, 39, 3772–3789). A review of the use of water as carrier phase for the catalyst may be found, for example, in B. Cornils, W. A. Herrmann (Eds.) "Aqueous-Phase Organometallic Catalysis", Wiley-VCH, Weinham, New York, Chichester, Brisbane, Singapore, Toronto, 1998, pages 352–361.

In hydrogenations in the gas phase, it is possible for other gases to be present in addition to hydrogen and substrate. For example, nitrogen and/or argon or alkanes which are gaseous under the hydrogenation conditions, for example methane, propane or butane, can be added to the hydrogenation gas or may already be present in the hydrogenation gas.

The hydrogenation in step b) of the process of the invention can be carried out continuously, semicontinuously or batchwise. Preference is given to a continuous process.

In step b) of the process of the invention, conversion of the 1,7-octadiene is preferably close to quantitative. However, the reaction can also be stopped after a partial conversion of the 1,7-octadiene of up to 70%, preferably up to 50%, particularly preferably up to 30%, very particularly preferably up to 20%. The selectivity of the hydrogenation can be increased considerably by partial conversion.

The main by-product in the hydrogenation of 1,7-octadiene to 1-octene is n-octane, and in addition, depending very much on the catalyst used, octenes and octadienes having internal as well as terminal double bonds are also formed.

The 1-octene is separated from the product mixture from the hydrogenation by distillation. If only part of the 1,7-octadiene is converted in the hydrogenation, the remaining 1,7-octadiene or a 1,7-octadiene-rich fraction is, in addition, wholly or partly separated off and is preferably returned to step b (hydrogenation) of the process.

The 1-octene obtained by the process of the invention can be used as comonomer in polymerization reactions of ethene or propene.

The present invention therefore also provides polyolefins obtained by copolymerization of at least one olefin with the 1-octene obtained by the process described.

Preferred polyolefins are polypropylene and polyethylene (i.e. ethene and propene are used as olefin). The proportion of the 1-octene obtained according to the invention is preferably 1–35%.

The polyolefins mentioned may further comprise additional monomers, e.g. EPDM, or can be copolymerized with one another (ethylene-propylene copolymers).

The following examples illustrate the invention without restricting its scope.

EXAMPLES

Example 1

Telomerization 186 g of formic acid, 400 g of N-methylpyrrolidone, 437 g of 1,3-butadiene, 1.3 g of palladium acetate and 3.0 g of triphenylphosphine were placed in a 3 liter autoclave (from Büchi) under protective gas. The autoclave was heated to 75° C. and the course of the reaction was followed by gas-chromatographic analysis of samples taken at regular intervals. After 120 minutes, the experiment was stopped by cooling to room temperature. According to GC analysis, 89% of the 1,3-butadiene had reacted, and the selectivity to 1,7-octadiene was 91.3%.

The 1,7-octadiene was separated from the other components by distillation.

Examples 2–4

Heterogeneously Catalyzed Hydrogenation

The hydrogenations were carried out in a 1 000 ml autoclave from Büchi.

The reaction mixture was analyzed by gas chromatography on a CP Wax 52 column from Chrompack. The catalyst H 14163, produced by Degussa AG, was used as catalyst. Its properties are described as follows by the manufacturer:

| | |
|---|---|
| Ru content | 1% by weight |
| Support | Alcoa F 1 (AlO(OH), Al(OH)$_3$) |
| Form | granules |
| Diameter | 1.6 mm |
| Bulk density | 0.93–1.09 g/cm$^3$ |

-continued

| BET surface area | 245 m²/g |
|---|---|
| Specific pore volume | 0.31 m²/g |

Example 2

10 g of the H14163 catalyst were placed in a catalyst basket of a 1 000 ml pressure reactor and 438 g of liquid 1,7-octadiene from example 1 were added. The. hydrogenation of. the 1,7-octadiene was carried out using pure hydrogen at a pressure of 10 bar and a temperature of 40° C. After 30 hours, the maximum yield of 1-octene of 41.6% had been reached. The main by-product formed was octane (26.8%). As further by-products, small amounts of 2-, 3- and 4-octene were also formed with a selectivity of 1.7%. After 95 hours, all of the 1,7-octadiene had been hydrogenated to octane.

Example 3

10 g of the catalyst were placed in the catalyst basket of a 1 000 ml pressure reactor and 438 g of liquid 1,7-octadiene from example 1 were added. The hydrogenation of the 1,7-octadiene was carried out using hydrogen containing 11 ppm CO at a pressure of 10 bar and a temperature of 40° C. After 53 hours, the maximum yield of 1-octene of 40.1% had been reached. The main by-product formed was octane (26.5%). As further by-products, small amounts of 2-, 3- and 4-octene were also formed with a selectivity of <2%.

Example 4

10 g of the catalyst were placed in the catalyst basket of a 1 000 ml pressure reactor and 438 g of liquid 1,7-octadiene from example 1 were added. The hydrogenation of the 1,7-octadiene was carried out using pure hydrogen at a pressure of 10 bar and a temperature of 60° C. After 31 hours, the maximum yield of 1-octene of 39.7% had been reached. The main by-product formed was octane (26.3%). As further by-products, small amounts of 2-, 3- and 4-octene were also formed with a selectivity of 3.3%.

The invention claimed is:

1. A process for preparing 1-octene, comprising:
   a) reacting 1,3-butadiene in the presence of a telomerization catalyst and a reducing agent, thereby forming 1,7-octadiene; and
   b) hydrogenating 1,7-octadiene, thereby forming 1-octene.

2. The process as claimed in claim 1, wherein the telomerization catalyst is a nickel, rhodium, palladium or platinum compound or a combination of these metal compounds.

3. The process as claimed in claim 2, wherein said metal compound or mixture of metal compounds is combined with at least one ligand.

4. The process as claimed in claim 3, wherein said ligand is a phosphine, a phosphinite, a phosphite, a phosphonite, an amine, a nitrile or a carbene.

5. The process as claimed in claim 1, wherein the reducing agent is formic acid, a formate, hydrogen or a combination thereof.

6. The process as claimed in claim 1, wherein the hydrogenation of said 1,7-octadiene is conducted in the presence of at least one element of transition metal Group VIII of the Periodic Table.

7. The process as claimed in claim 6, wherein the hydrogenation of said 1,7-octadiene is conducted to a conversion of 70%.

8. The process as claimed in claim 7, wherein the remaining unconverted 1,7-octadiene is wholly or partly separated from the hydrogenated material and is then wholly or partly returned to the hydrogenation step (b).

9. The process as claimed in claim 1, wherein the 1,3-butadiene reactant is a 1,3-butadiene mixture with other $C_4$-hydrocarbons.

10. The process as claimed in claim 2, wherein the palladium compound catalyst is selected from the group consisting of palladium(II) chloride, palladium(II) bromide, palladium(II) acetate, palladium(II) formate, palladium(II) octanoate, palladium(II) carbonate, palladium(II) sulfate, palladium(II) nitrate, palladium(II) acetylacetonate, palladium(II) alkylsulfonate, $Na_2PdCl_4$, $K_2PdCl_4$, dichlorobis(benzonitrile)palladium, allylpalladium chloride, allylpalladium acetate, trisallylpalladium, 1,5-cyclooctadienepalladium(II) chloride, bis(triphenylphosphine) palladium(II) chloride or 1,2-bis(diphenylphosphino)palladium(II) chloride.

11. The process as claimed in claim 1, wherein said telomerization catalyst is present in the reaction in an mount of 0.1 to 50,000 ppm of metal based on the amount of reaction mixture.

12. The process as claimed in claim 4, wherein said phosphine is tris(o-tolyl)phosphine, tris(y-methoxyphenyl)phosphine, tris(p-dimethylaminophenyl)phosphine, tricyclohexylphosphine, tricyclopentylphosphine, trisethylphosphine, tris(1-naphthyl)phosphine, tribenzylphosphine, tri-n-butylphosphine, tri-tert-butylphosphine, tris-(3-sulfonatophenyl)phosphine (metal salt) or (3-sulfonatophenyl)diphenylphosphine (metal salt); said phosphite is trimethylphosphite, triethylphosphite, tri-n-propylphosphite, tri-iso-propylphosphite, tri-n-butylphosphite, tri-iso-butylphosphite, tri-tert-butylphosphite, tris(2ethylhexyl)phosphite, triphenylphosphite, tris(2,4-di-tert-butylphenyl)phosphite, tris(2-tert-butyl-4-methoxyphenyl)phosphite, tris(2-tert-butyl-4-methylphenyl)phosphate or tris(p-cresyl)phosphate; said phophonite is methyldiethoxyphosphine, phenyldimethoxyphosphine, phenyldiphenoxyphosphine or 2-phenoxy-2H-dibenz[c,e][1,2]oxaphosphorin and derivatives thereof in which some or all of the hydrogen atoms are replaced by alkyl and/or aryl radicals or halogen atoms; said phosphinite is diphenyl(phenoxy)phosphine or derivatives thereof in which or all of the hydrogen atoms are replaced by alkyl and/or aryl radicals or halogen atoms, diphenyl(methoxy)phosphine or diphenyl(ethoxy)phosphine or said carbene is 1,3-disubstituted-2,3-dihydro-1H-imidazol-2-ylidene or 1,3-disubstituted-4,5-dihydro-1H-triazol-5-ylidene or 2,3-dihydrotriazol-2-ylidene.

13. The process as claimed in claim 3, wherein the ratio of ligand to metal ranges from 0.1 to 500/1.

14. The process as claimed in claim 5, wherein the formate compound is ammonium formate, trimethylammonium formate, triethylammonium formate, tripropylammonium formate or an alkali or alkaline earth metal formate salt.

15. The process as claimed in claim 1, which further comprises conducting the telomerization step in the presence of a base which is an alkali metal or an alkaline earth metal hydroxide, an alkali metal or an alkaline earth metal carbonate or hydrogencarbonate, a quaternary or phosphonium hydroxide, an alkoxide, an enolate, a phenoxide, a metal salt of a carboxylic acid, a metal amide, an alkali metal borohydride, an alkali metal aluminum hydride or an organic nitrogen base.

* * * * *